United States Patent [19]

de Ruiter

[11] Patent Number: Plant 7,362

[45] Date of Patent: Oct. 23, 1990

[54] HYBRID TEA ROSE PLANT NAMED RUIDRIKO

[75] Inventor: Gijsbert de Ruiter, Hazerswoude, Netherlands

[73] Assignee: de Ruiter's Nieuwe Rozen B.V., Hazerswoude, Netherlands

[21] Appl. No.: 392,566

[22] Filed: Aug. 11, 1989

[51] Int. Cl.[5] ..... A01H 5/00

[52] U.S. Cl. ..... Plt./18

[58] Field of Search ..... Plt./18

*Primary Examiner*—James R. Feyrer

*Attorney, Agent, or Firm*—Christie, Parker & Hale

[57] ABSTRACT

A new variety of hybrid tea rose having light pink flowers with long vase-life and lasting quality produced on a plant suitable for growing under glass.

2 Drawing Sheets

SUMMARY OF THE INVENTION

The present invention relates to a new and distinct variety of rose plant of the hybrid tea rose class, which was originated by me by crossing, as seed parent the variety known as "Korflug" and as pollen parent, the variety known as "Ruimeva". The varietal denomination of this new rose is "Ruidriko".

Among the novel characteristics possessed by this new variety which distinguishes it from its parents and all other varieties of which I am aware are its attractive light pink flowers borne on a plant particularly suited for growing under glass to produce cut flowers. "Ruidriko" can be reproduced through propagation by cuttings, budding, grafting and micropropagation. Flowers of the new variety are long lasting on the plant and have long vase-life as cut flowers. Asexual reproduction by budding and grafting and by propagation by cuttings of the new variety as performed in Hazerswoude, Holland, shows that the foregoing and other distinguishing characteristics come true to form and are established and transmitted through succeeding propagations.

The accompanying drawings show typical specimens of the vegetative growth and flowers of the new variety in different stages of development and depicted in color as nearly true as it is reasonably possible to make the same in color illustrations of this character. However, the color representation in the illustration of details of the new variety in FIG. 1 are more accurate and the illustration of cut flowers in FIG. 2 is intended to show the excellent form of the new variety.

BRIEF DESCRIPTION OF THE DRAWINGS

FIG. 1 is an illustration showing details of the new rose variety, "Ruidriko"; and FIG. 2 is an illustration of cut flowers of the new variety to illustrate flower form.

DESCRIPTION OF PREFERRED EMBODIMENT

The following is a detailed description of my new variety, with color terminology in accordance with The Royal Horticultural Society Colour Chart (RHSCC) and horticultural terminology in accordance with standard terminology used in UPOV-approved horticultural guidelines. The terminology used in color descriptions herein refers to plate numbers in the aforementioned color chart.

Parentage: Seedling.

*Seed patent.*—"Korflug".

*Pollen parent.*—"Ruimeva".

Class: Hybrid tea.

As can be seen in the accompanying illustrations, FIG. 1 shows details of the new variety "Ruidriko". In the illustration there is shown the top of a young shoot 1; examples of foliage as compound three, five and seven leaflet leaves, 2, 3 and 4, respectively, a stem 5; flower buds, 6, after sepals fall and, 7, after petals begin to unfurl; a flower, 8, about one-third to one-half open; and a flower 9, fully open. Also shown are flower stems 10, 11 and 12, with reproductive organs but without petals.

FIG. 2 shows specimens of cut flowers of "Ruidriko" showing the appealing exhibition form of this variety.

The following further horticultural observations were made of specimens grown outdoors in Holland.

FLOWER

Blooming habit: Nearly continuous.

A. Bud:

(1) *Size.*—Medium.

(2) *Form.*—Pointed, ovate.

(3) *Color.*—As sepals divide, bud color is near 49D infused with off-white coloring.

(4( *Sepals.*—Not longer than bud, simple.

(5) *Peduncle.*—Length — about 12–13 cm; aspect — straight; strength — erect; color — medium green.

B. Bloom:

*Flower.*—Large; viewed from top-rounded; viewed from side (A) upper part of fully opened flower — flattened convex, (B) lower part of fully opened flower — flattened convex.

(1) *Size.*—Average size when fully expanded — about 14 cm.

(2) *Borne.*—Primarily, singly, one to a stem.

(3) *Form.*—Ovoid at first, becoming flat to convex. Petals reflex and quill to points.

(4) *Petalage.*—Number of petals under normal conditions — about 24–28, fully double.

(5) *Color.*—After sepals fall, visible petal under surface is near 49D to 56 C, D with pale off-white infusion but deeper pink at center where petals bunch; as petals begin to unfurl, petal top surface is near 56B to C and under-surface is a little lighter 56D to 39D. As flower opens, color of petal top surface becomes in the range of 56C to 39C-D. Petals at point of attachment are near 2C. Overall tonality from a distance is an attractive creamy light pink.

(6) *Pedicel.*—Few hairs or prickles.

(7) *Lasting quality.*—Very long lasting on plant and as cut flower; long vase-life.

C. Petals:

(1) *Texture.*—Medium to thick.

(2) *Appearance.*—Inside velvety and outside satiny.

(3) *Form.*—Broad obovate.

(4) *Arrangement.*—Regularly arranged, imbricated.

(5) *Petaloids in center.*—Few to none.

(6) *Persistence.*—Drop off cleanly.

(7) *Fragrance.*—Slight to none.

(8) *Size.*—Very large.

REPRODUCTIVE ORGANS

A. Stamens, filaments and anthers:

*Arrangement and color.*—Regularly arranged around styles. Filaments — pale translucent with yellow top.

B. Pollen:

*Color.*—yellow.

C. Styles: Long, bunched, upper half medium hairiness.

D. Stigma: Full, thick, below anthers.

E. Hips: Large, pitcher-shaped.

PLANT

A. Form: Upright bushy.

B. Growth: Vigorous.

C. Foliage: Compounds 3, 5 and 7 leaflets.

(1) *Size.*—Small to medium leaves.

(2) *Quantity.*—Abundant.

(3) *Color.*—Foliage at time of first flowering — dark green.

(4) *Shape.*—Oval, pointed.

(5) *Texture.*—Upper side is weakly glossy; under side is matte.

(6) *Edge.*—Serrate.

(7) *Serration.*—Ordinary, acuminate apices.

(8) *Leaf stem.*—Color — medium to dark green.

(9) *Stipules.*—Medium length, slightly bearded, light green, distinct auricle.

(10) *Leaflet.*—Cross section — flat Terminal leaflet — short, narrow, rounded base. Petiole — medium.

D. Wood:

(1) *New wood.*—Color — green with reddish brown.

(2) *Old wood.*—Color — medium green.

E. Prickles (thorns):

(2) *Prickles.*—Present, quantity (main stalk) — ordinary; on laterals from stalk — few; form — mainly straight, some slanted slightly downward; shape of upper side — concave; shape of lower side — concave; length — very few $\leqq 5$ mm, medium; number $> 5$ mm; color — tan to light pink; position — irregular.

F. Winter hardiness: Needs protection outdoors in severe climates.

I claim:

1. A new and distinct variety of rose plant of the hybrid tea rose class, substantially as shown and described, characterized particularly by a plant suitable for growing under glass and which produces long lasting attractive light pink flowers.

* * * * *

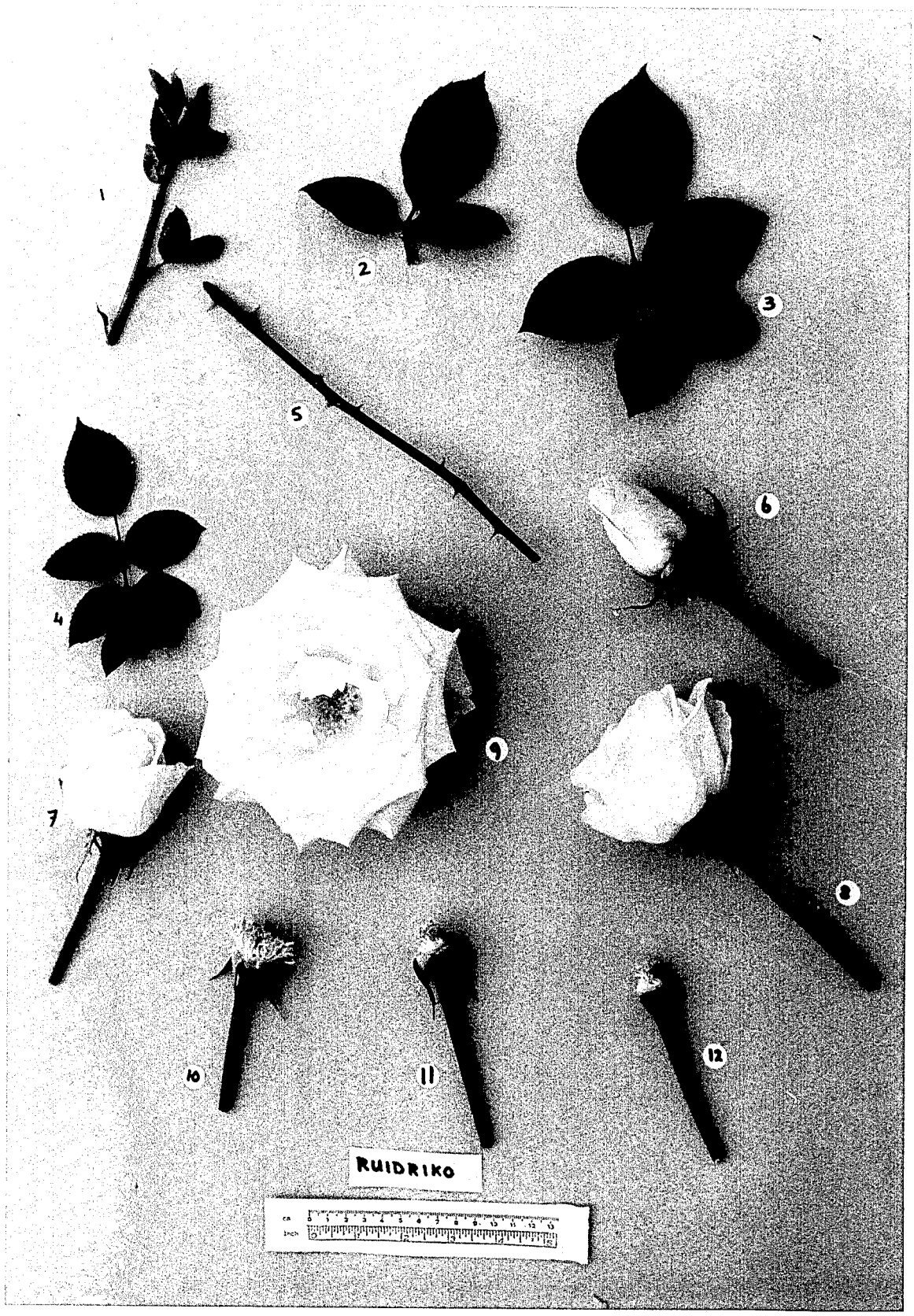
1
2
3
4
5
6
7
8
9
10
11
12
RUIDRIKO

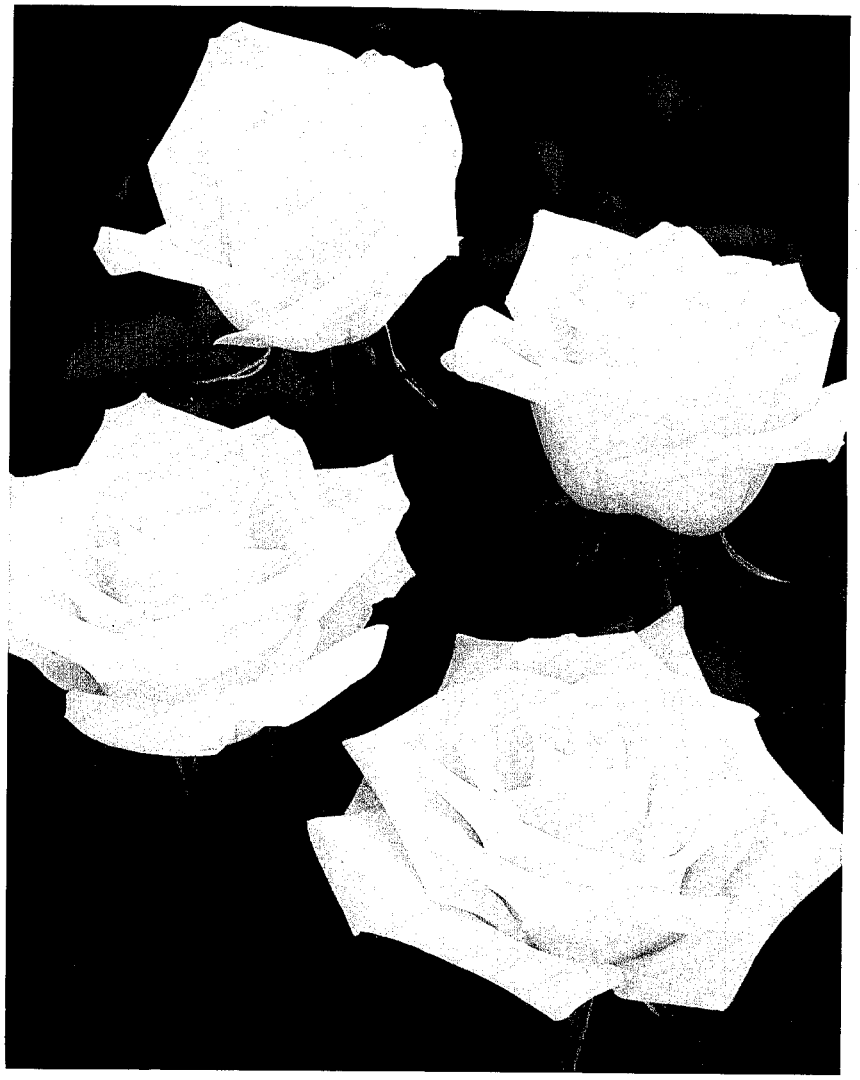

UNITED STATES PATENT AND TRADEMARK OFFICE

CERTIFICATE OF CORRECTION

PATENT NO. : Plant 7,362

DATED : October 23, 1990

INVENTOR(S) : Gijsbert de Ruiter

It is certified that error appears in the above-identified patent and that said Letters Patent is hereby corrected as shown below:

ON TITLE PAGE:

[73] Assignee, change "de Ruiter's Nieuwe Rozen B.V." to -- De Ruiter's Nieuwe Rozen B.V. --.

Column 2, line 20, insert "1." before "FLOWER".
Column 2, line 27, change "(4(" to -- (4) --.

Column 3, line 17, Insert "2." before "REPRODUCTIVE ORGANS".
Column 3, line 30, Insert "3." before "PLANT".

Column 4, line 19, delete "(2)" and insert -- (1) --.

Signed and Sealed this

Twenty-third Day of June, 1992

*Attest:*

DOUGLAS B. COMER

*Attesting Officer*

*Acting Commissioner of Patents and Trademarks*